United States Patent
Mansour et al.

(10) Patent No.: US 10,041,124 B2
(45) Date of Patent: Aug. 7, 2018

(54) METHYLATION BIOMARKERS FOR OVARIAN CANCER

(71) Applicant: King Abdullah University of Science and Technology, Thuwal (SA)

(72) Inventors: Hicham Mansour, Thuwal (SA); Roberto Incitti, Thuwal (SA); Vladimir Bajic, Thuwal (SA)

(73) Assignee: King Abdullah University of Science and Technology, Thuwal (SA)

( * ) Notice: Subject to any disclaimer, the term of this patent is extended or adjusted under 35 U.S.C. 154(b) by 578 days.

(21) Appl. No.: 14/153,651

(22) Filed: Jan. 13, 2014

(65) Prior Publication Data
US 2014/0199696 A1      Jul. 17, 2014

Related U.S. Application Data

(60) Provisional application No. 61/752,156, filed on Jan. 14, 2013.

(51) Int. Cl.
*C12Q 1/68*      (2018.01)
*C12Q 1/6886*   (2018.01)

(52) U.S. Cl.
CPC ..... *C12Q 1/6886* (2013.01); *C12Q 2600/154* (2013.01)

(58) Field of Classification Search
None
See application file for complete search history.

(56) References Cited

PUBLICATIONS

Huang et al. in view of Teodoridis et al., Menedez et al., Gloss et al., Dai et al., Howard et al., Su et al., and Sakuma et al.*
Teodoridis et al. (Proceedings of the American Association for Cancer Research Annual Meeting, (Mar. 2004) vol. 45, pp. 1153. Meeting Info.: 95th Annual Meeting of the American-Association-for-Cancer-Research. Orlando, FL, USA. Mar. 27-31, 2004. Amer Assoc Canc Res.).*
Menedez et al.( Molecular Cancer 2007, 6:10, nine pages).*
Gloss et al. (Cancer Letters 318 (2012) 76-85).*
Dai et al. (Clin Cancer Res; 17(12); 4052-62).*
Howard et al. (Proceedings of the American Association for Cancer Research Annual Meeting, (Apr. 2006) vol. 47, pp. 605. Meeting Info.: 97th Annual Meeting of the American-Association-for-Cancer-Research (AACR). Washington, DC, USA. Apr. 1-5, 2006. Amer Assoc Canc Res.).*
Su et al. (Int. J. Cancer: 124, 387-393 (2009)).*
Sakuma et al.(Cancer Sci 2007; 98: 380-386).*
Melnikov et al. (Journal of Molecular Diagnostics, vol. 11, No. 1, Jan. 2009, pp. 60-65).*
Costello et al. Journal of Biological Chemistry. vol. 269, No. 25, Issue of Jun. 24, pp. 1722g-17237, 1994.*
Hesselink et al. Clin Cancer Res 2011; 17:2459-2465.*
van Eijk et al. BMC Genomics 2012, 13:636, thirteen pages.*
Wu J Pathol 2001; 195: 53-65.*
Newton et al (2001) Journal of Computational Biology, vol. 8, No. 1, 2001, pp. 37-52.*
Slonin, Nature Genetics Supplement, vol. 32, Dec. 2002, pp. 502-508.*
Baker. Journal of the National Cancer Institute, vol. 95, No. 7, Apr. 2, 2003.*
Whitehead (Genome Biology 2005 vol. 6 Issue 2 Article R13).*
Bock (Epigenomics 2009 vol. 1 No. 1 pp. 99-110).*
Michels (Experimental Gerontology 2010 vol. 45 pp. 297-301).*
Cottrell, S., CLI, Oct. 2005.
Kobayashi, E., et al., Cancer Epidemiol Biomarkers Prev., Oct. 12, 2012.
Angelopoulou, K. et al., Clin Biochem 33:53-62 (2000).
Bast, R.C. et al., Int J Gynecol Cance6r 15 (suppl 3):274-281 (2005).
Bowen, N.J., et al., BMC Genomics Dec. 29;2:71 (2009).
Clark-Pearson, D.L., N. Engl J Med 361:170-177 (2009).
Cottrell, S., Cli, Oct. (2005), Molecular Diagnostic applications of DNA methylation technology. two pages.
Gregorakis A.K., et al., Prostate, 68:759-765 (2008).
Harpio R., et al., Clin Biochem, 37: 512-518 (2004).
Hoskins, W. J., J Cell Biochem; 23 (suppl):189-199 (1995).
Kobayashi, E., et al., Cancer Epidemiol Biomarkers Prey., Oct. 12, 2012. vol. 21 No. 11 p. 1902-1912.
Lili, L.N, et al., www.ncbi.nlm.nih.gov/geo/query/acc.cgi?acc=GSE38666 Jun. 12, 2012.
Maldonado L, et al. Biomark Med Aug.;4(4):543-70 (2010).
Memarzadeh, S., et al., J Reprod Medicine, 46:621-629 (2001).
Nossov V, et al., Am J Obstet Gynecol, 199: 215-223 (2008).
Rein et al. Nucleic Acids Res, 26, 2255 (1998).
Seeber, L.M., et al., Methods Mol Biol; 863:253-69 (2012).
Thorpe, J D, et al., PLoS One, 2: e1281 (2007).
Weiland F., et al., Int J Mol Sci 25; 13(8): 10568-82 (2012).
Yoshimasu, T, et al., Int J Biol Markers, 14:99-105 (1999).

\* cited by examiner

*Primary Examiner* — Juliet C Switzer
(74) *Attorney, Agent, or Firm* — Pabst Patent Group LLP

(57) ABSTRACT

Different combinations of methylation status based biomarkers can be used to test for ovarian cancer with high sensitivity and high specificity.

2 Claims, No Drawings

US 10,041,124 B2

METHYLATION BIOMARKERS FOR OVARIAN CANCER

CLAIM OF PRIORITY

This application claims priority to U.S. Provisional Patent Application No. 61/752,156, filed on Jan. 14, 2013, which is incorporated by reference in its entirety.

TECHNICAL FIELD

This invention relates to methylation biomarkers for ovarian cancer.

BACKGROUND

Ovarian cancer (OC) is one of the deadliest cancers in women. It is frequently found in asymptomatic patients until it reaches an advanced and untreatable stage (metastasis stage). Serum cancer antigen-125 (CA-125) has been extensively investigated over the last 30 years and is clinically one of the most reliable serum markers for ovarian cancer. However, on its own, this marker has low sensitivity and specificity. It can be undetectable or showing low quantity in serum and therefore miss half of early-stage patients that have still-treatable tumors. The situation is similar for two other ovarian cancer biomarkers, E2F5 and AP2.

SUMMARY

Testing the methylation status of a combination of several genes provides a highly sensitive and highly specific non-invasive tumor diagnosis for ovarian cancer. This test can be carried out at low-cost tests using easily obtained samples such as blood, serum, plasma, saliva, or urine.

In one aspect, a highly specific and highly selective method of detecting ovarian cancer in a patient includes: obtaining a DNA sample from the patient; and measuring, from the DNA sample, a methylation level in a regulatory region of each of a plurality of genes selected from the group consisting of: CYP39A1, DAPK1, CAV1, ARMCX1, ROCK1, CDKN1B, MLH1, MED1, PEG3, BEX4, SFRP1, CCND2, SPARCL1, ARMCX2, PLAGL1, RAD51C, SOCS2, RARRES1, UCHL1 and DIRAS3.

The method can further include comparing the measured methylation level for each of the plurality of genes to a respective threshold methylation level, and, based on the comparisons, detecting the presence or absence of ovarian cancer in the patient with high sensitivity and high specificity. Our methodology suggests that, based on the prediction of methylation profiles, the presence or absence of ovarian cancer can be detected with a sensitivity greater than 90% and a specificity greater than 90%, sensitivity greater than 95% and a specificity greater than 95%, or with a sensitivity greater than 97% and a specificity greater than 99%.

The plurality of genes can include five or more of the genes listed above. The DNA sample can be obtained from a body fluid, wherein the body fluid is blood, serum, plasma, saliva, urine, stool, tissue, or a combination thereof.

The genes can be the genes of OC Set 1: CYP39A1, DAPK1, CAV1, ARMCX1, ROCK1, MED1, SFRP1, and CCND2. The genes can be the genes of OC Set 2: CYP39A1, DAPK1, CAV1, ARMCX1, ROCK1, PEG3, SFRP1, and CCND2. The genes can be the genes of OC Set 3: CYP39A1, DAPK1, CAV1, ARMCX1, and ROCK1. The genes can be the genes of OC Set 4: CYP39A1, DAPK1, CAV1, ARMCX1, and CDKN1B. The genes can be the genes of OC Set 5: CYP39A1, DAPK1, CAV1, ARMCX1, and MLH1. The genes can be the genes of OC Set 6: CYP39A1, DAPK1, CAV1, ARMCX1, and MED1. The genes can be the genes of OC Set 7: CYP39A1, DAPK1, CAV1, ARMCX1, and BEX4.

Other aspects, embodiments, and features will be apparent from the following description, the drawings, and the claims.

DETAILED DESCRIPTION

Cancer is a class of diseases in which a group of cells (tumor cells) display uncontrolled growth, invasion, and sometimes metastasis. Ovarian cancer is a type of cancer that forms in tissues of the ovary. Examples of ovarian cancers include, but are not limited to ovarian epithelial carcinoma and germ cell tumors.

While ovarian cancer accounts for only one third of gynecologic cancers, it results in 55% of deaths from gynecologic malignancies and 6% of all cancer deaths in women (Memarzadeh S, Berek J S., J Reprod Medicine 2001, 46:621-629; Hoskins W J. J Cell Biochem 1995; 23 (suppl):189-199, which is incorporated by reference in its entirety). Long-term survival has not changed significantly in the last three decades, largely due to inadequate diagnostic approaches that only detect well-established cancers. Only 19% of ovarian cancers are diagnosed at Stage I (Hoskins W J., J Cell Biochem 1995, 23 (suppl):189-199, which is incorporated by reference in its entirety), while other cancers associated with women are primarily diagnosed at Stage I (77% of endometrial cancers, 55% of breast cancers and 83% of cervical cancers). Since Stage I ovarian cancer can be cured in 90% of cases, but five-year survival for advanced disease (Stage III and IV) is less than 21%, prospects for significant improvement in survival reside in early diagnosis of disease. Current diagnostic approaches exhibit several deficiencies (Clark-Pearson D L., N Engl J Med 2009, 361:170-177, which is incorporated by reference in its entirety). First, most biomarkers lack cancer specificity. Second, most biomarkers lack positive predictive value for early stage disease. Third, most biomarkers are unstable in the peripheral circulation.

While intended as a disease monitor (defining therapeutic responses, disease recurrence and progression) (Nossov V, Amneus M, Su F, Lang J, Janco J M T, Reddy S T, Farias-Eisner R., Am J Obstet Gynecol 2008, 199: 215-223, which is incorporated by reference in its entirety), the assessment of circulating CA125 has been used to diagnose ovarian cancer (Bast R C, Badgwell D, Lu Z, Marquez R, Rosen D, Liu J, Baggerly K A, Atkinson E N, Skates S, Zhang Z, Lokshins A, Menon U, Jacobs I, Lu K., Int J Gynecol Cancer 2005, 15 (suppl 3): 274-281, which is incorporated by reference in its entirety). CA125 is neither sensitive nor specific for de novo ovarian cancer detection, since it is elevated in less than 50% of women with stage I disease. CA125 has poor specificity, which is shown by its elevation in benign and malignant breast and colon disease, peritoneal irritants, and benign gynecologic diseases, among others (Bast R C, Badgwell D, Lu Z, Marquez R, Rosen D, Liu J, Baggerly K A, Atkinson E N, Skates S, Zhang Z, Lokshins A, Menon U, Jacobs I, Lu K., Int J Gynecol Cancer 2005, 15 (suppl 3): 274-281, and Kobayashi E, Ueda Y, Matsuzaki S, Yokoyama T, Kimura T, Yoshino K, Fujita M, Kimura T, Enomoto T. Biomarkers for Screening, Diagnosis, and Monitoring of Ovarian Cancer. Cancer Epidemiol Biomarkers Prev. 2012 Oct. 12. Weiland F, Martin K, Oehler M K, Hoffmann P. Int J Mol Sci. Deciphering the Molecular Nature of Ovarian Cancer Biomarker CA125. 2012; 13(8): 10568-82, each of which is incorporated by reference in its entirety). Due to CA125's limited expression in early stage ovarian cancers and its association with nonmalignant pathologies, CA125, at best, exhibits a positive predictive value of 57% (Nossov V, Amneus M, Su F, Lang J, Janco J M T, Reddy S T, Farias-Eisner R., Am J Obstet Gynecol 2008, 199: 215-223, which is incorporated by reference in its entirety).

Complicating the lack of specificity of current diagnostic methods is the poor stability of many biomarkers within the peripheral circulation. For antigen-based assays, such as CA125 ELISA and even SELDI-TOF-MS, once the target antigens are released from the tumor, they must saturate the immunologic antigen-processing capacity, intravasate, and reach a detectable steady-state concentration in the circulation. As a result, circulating biomarker concentrations are influenced by multiple variables, such as marker intravasation, clearance rates and protein half-lives in the blood. While stabilities of all biomarkers have not been investigated, studies on circulating p53 indicate a half-life of several hours (Angelopoulou K, Yu H, Bharaj B, Giai M, Diamandis E P., Clin Biochem 2000, 33: 53-62, which is incorporated by reference in its entirety) and the half-life of circulating S100B protein (in melanoma) has been estimated to be only 30 minutes (Harpio R, Einarsson R., Clin Biochem 2004, 37: 512-518, which is incorporated by reference in its entirety). In prostate cancer, total PSA and free PSA exhibit a rapid exponential degradation phase with a half-life of 4.27 and 2.14 hours, respectively (Gregorakis A K, Stefanakis S, Malovrouvas D, Petraki K, Gourgiotis D, Scorilas A., Prostate 2008, 68:759-765, which is incorporated by reference in its entirety). In patients with intrathoracic tumors, the average half-lives of CEA, SCC, TPA and CYFRA were 36 hours, 2.2 hours, 2.5 hours and 1.5 hours, respectively (Yoshimasu T, Maebeya S, Suzuma T, Bessho T, Tanino H, Arimoto J, Sakurai T, Naito Y., Int J Biol Markers 1999, 14:99-105, which is incorporated by reference in its entirety). In addition to short half-lives, some serum biomarkers for ovarian cancer have also been demonstrated to be highly sensitive to confounding factors, including psychological stress, time of blood draw, and uncontrolled differences in sample manipulation (Thorpe J D, Duan X, Forrest R., PLoS ONE 2007, 2: e1281, which is incorporated by reference in its entirety).

As discussed above, screening tests for cancer, particularly ovarian cancer, based on currently known biomarkers have low sensitivity and low specificity, and few of such tests are evaluated on body fluids. New combinations of biomarkers, in particular methylation biomarkers, can be tested on readily and easily obtained body fluid samples to screen for ovarian cancer with high sensitivity and high specificity.

Sensitivity refers to the ability of a screening test to correctly identify true positives. For example, sensitivity can be expressed as a percentage, the proportion of actual positives which are correctly identified as such (e.g., the percentage of test subjects having cancer correctly identified by the test as having cancer). A test with high sensitivity has a low rate of false negatives.

Specificity refers to the ability of a screening test to correctly identify true negatives. For example, specificity can be expressed as a percentage, the proportion of actual negatives which are correctly identified as such (e.g., the percentage of test subjects not having cancer correctly identified by the test as not having cancer). A test with high specificity has a low rate of false positives.

Using a test based on a combination of biomarkers provides a screening test for ovarian cancer that can have higher sensitivity, higher specificity, or both higher sensitivity and higher specificity, than tests based on a single biomarker. Preferably a screening test has high levels of both sensitivity and specificity.

Alterations of DNA methylation patterns have been recognized as a common change in human cancers. Aberrant methylation of normally unmethylated CpG islands in or near the promoter region of many genes has been associated with transcriptional inactivation of important genes, including tumor suppressor genes, DNA repair genes, and metastasis inhibitor genes. Therefore, detection of aberrant promoter methylation of cancer-related genes can be an efficient method for the diagnosis, prognosis and/or detection of tumors.

A challenge in identifying DNA methylation patterns is that 5-methylcytosine is indistinguishable from cytosine in its hybridization behavior. The specific reaction of bisulfite with cytosine is therefore useful in investigating DNA methylation. Bisulfite can convert cytosine, but not 5-methylcytosine, to uracil. Uracil corresponds in its base-pairing behavior to thymidine, and thus allows 5-methylcytosine to be differentiated from cytosine using "standard" molecular biological techniques, for example, by amplification and hybridization or sequencing.

An older method incorporates the DNA to be investigated in an agarose matrix, through which diffusion and renaturation of the DNA is prevented (bisulfite reacts only on single-stranded DNA) and all precipitation and purification steps are replaced by rapid dialysis. Individual cells can be investigated with this method, which illustrates the potential of the method. Of course, previously, only individual regions of up to approximately 3000 base pairs in length have been investigated; a global investigation of cells for thousands of possible methylation analyses is not possible. Of course, this method also cannot reliably analyze very small fragments of small sample quantities. These are lost despite the protection from diffusion through the matrix. Other known methods for detecting 5-methylcytosines are described by Rein et al. (Nucleic Acids Res. 1998, 26, 2255, which is incorporated by reference in its entirety) and Cottrell (Cottrell, S., Molecular diagnostic applications of DNA methylation technology, CLI October 2005, which is incorporated by reference in its entirety).

Techniques such as methylation-specific arbitrarily primed PCR, methylated CpG island amplification (MCA), differential methylation hybridization (DMH), and restriction landmark genomic scanning (RLGS) take advantage of methylation-specific restriction enzymes to scan the genome for aberrantly methylated CpG sites. The advantage of these methods is that they directly look for methylation differences. In contrast, candidates can also be identified indirectly using gene expression studies. Gene expression in cell lines treated with 5-azacytidine can be compared to mock-treated cell lines to find genes activated by this de-methylating agent. Some genes in the literature, such as known tumor suppressor genes with CpG islands, are also good candidates.

Further analysis of these marker candidates requires higher throughput methodology. By far the most commonly used assay in research labs is methylation specific-PCR (MSP) or the real-time version (MethyLight). The sample DNA is treated with sodium bisulphite to convert unmethylated cytosines to uracils, while methylated cytosines remain intact. In a gel based MSP assay, one set of primers amplifies the unmethylated version and one set amplifies the methylated version, and the presence of a band on a gel in each reaction determines the methylation state. In the real-time version, amplification with methylation specific primers with or without probes is normalized to the total amount of input DNA to determine the fraction of DNA methylated for each region of interest. Alternative marker analysis methods include oligonucleotide arrays, primer extension, and sequencing.

Biomarkers for ovarian cancer were identified in the following way. Public gene expression data for normal and ovarian cancer cells was mined to identify genes showing reduced expression levels in ovarian cancer cells compared to normal cells. Those genes having reduced expression levels in ovarian cancer and CpG promoter islands were further investigated. It is generally known that reduced expression levels for genes with CpG islands is correlated with increased methylation in the CpG islands. For each of the genes selected for further investigation, a quantitative correlation between expression level and extent of methylation was established. Then, based on that quantitative correlation, a threshold methylation level was predicted for each gene. The threshold level was set as the highest extent of methylation seen in the normal samples, plus an additional amount, e.g., 5%, 10%, 25%, 33%, etc.

The predictive value of these biomarkers was tested. Again, methylation levels of the genes was determined for a group of normal samples and ovarian cancer samples, based on publicly available expression data and the quantitative correlation of methylation level and gene expression. For each gene in each sample, the methylation level was compared to the methylation threshold for that gene. If the methylation level was higher than the threshold, that gene was scored as "true" (i.e., predictive of the presence of cancer) for that sample, or, if the methylation level was below the threshold, that gene was scored as "false" (i.e., predictive of the absence of cancer) for that sample. The sensitivity and specificity of several suitably chosen combinations of genes, for correctly predicting the presence or absence of cancer, was then determined based on the scores as defined above.

Thus, in clinical use, the biomarkers can be used in the following way. A DNA sample is obtained from a subject. The DNA sample can be derived from any suitable source, including but not limited to blood, serum, plasma, saliva, urine, stool, tissue, or a combination of these. Preferably the DNA sample is derived from a source other than tissue; e.g., blood, serum, plasma, saliva, or urine. The methylation status of several of the biomarker genes identified in the manner described above is then tested by any suitable method for determining the extent of DNA methylation, including but not limited to methylation specific PCR; methylated CpG island amplification; differential methylation hybridization; or restriction landmark genomic scanning. Advantageously, the assessment of methylation is a very stable procedure since, unlike, e.g., measuring mRNA levels, it is much less influenced by experimental parameters. This makes the test efficient for use by any clinical laboratory. The experimentally determined methylation levels for each gene are first compared to their respective threshold levels, and scored as true or false. Advantageously, by using a combination of biomarkers instead of a single marker, the result of the test is both highly sensitive and highly specific. The results of our study show that the test has the potential to have: a/ a sensitivity of no less than 90%, no less than 95%, no less than 96%, no less than 97%; b/ a specificity of no less than 90%, no less than 95%, no less than 96%, no less than 97%, no less than 98%, no less than 99%, or 100%; and c/ in some instances, both sensitivity and specificity can be no less than 90%, no less than 95%, no less than 96%, no less than 97%.

Various epigenetic changes including CpG island methylation have been identified in ovarian cancer (Seeber L M, van Diest P J., Epigenetics in ovarian cancer, Methods Mol Biol. 2012; 863:253-69, which is incorporated by reference in its entirety). It is now recognized that in addition to genetic alterations, epigenetic mechanisms, such as DNA methylation, histone modifications and nucleosome remodeling, play an important role in the development and progression of ovarian cancer by modulating chromatin structure, and gene and miRNA expression (Maldonado L, Hogue M O., Epigenomics and ovarian carcinoma, Biomark Med. 2010 Aug. 4(4):543-70, which is incorporated by reference in its entirety). In addition to having a plausible role in genomic instability during OC development, the methylation pattern of a few suitably chosen genes could be used to screen and detect patients having different stages of OC. Most importantly, methylation tests can be done using body fluids such as serum, urine, vaginal smear and others.

Using a new computational methodology and available public data, a set of biomarkers—methylated promoter regions of a set of genes—for ovarian cancer were identified and then validated in different combinations. The genes were known and some have been previously identified as biomarkers for cancers, but the set, and the combinations of genes from within the set, are new.

Genes whose predicted combined methylation patterns provide greater than 90% sensitivity and 100% specificity for OC diagnosis were identified based on a data set of 37 OC patients and 32 OC-free individuals. Subsets of these genes can also provide predicted greater than 90% sensitivity and 100% specificity for OC diagnosis. These predicted methylation pattern combinations have never been described before for the screening, or diagnosis or prognosis of OC. Transcriptomic data is largely published and made available. However, since methylation technologies are relatively recent, relatively little full methylation public data is available for body fluids as yet. With the goal of identifying a set of methylation-based biomarkers affording non-invasive screening, diagnosis and prognosis of OC, an inferred correlation between gene expression profile in tissue and methylation of these genes in serum was used. This correlation was then applied to assess in silico the sensitivity and specificity of gene markers already published as being methylated in OC. This method allows the identification of a set of genes with a strong diagnostic power when used in combination even at high thresholds of the methylation.

The base set of genes identified is as follows:

OC Base Set: CYP39A1 (NCBI Gene ID: 51302), DAPK1 (Gene ID:1612), CAV1 (Gene ID:857), ARMCX1 (Gene ID:51309), ROCK1 (Gene ID:6093), CDKN1B (Gene ID:1027), MLH1 (Gene ID:1027), MED1 (Gene ID:5469), PEG3 (Gene ID:5178), BEX4 (Gene ID:56271), SFRP1 (Gene ID:6422), CCND2 (Gene ID:894), SPARCL1 (Gene ID:8404), ARMCX2 (Gene ID:9823), PLAGL1 (Gene ID:5325), RAD51C (Gene ID:5889), SOCS2 (Gene ID:8835), RARRES1 (Gene ID:5918), UCHL1 (Gene ID:7345) and DIRAS3 (Gene ID:9077).

The set of the regulatory regions of the following genes will be called OC Set1: CYP39A1, DAPK1, CAV1, ARMCX1, ROCK1, MED1, SFRP1, and CCND2.

The set of the regulatory regions of the following genes will be called OC Set2: CYP39A1, DAPK1, CAV1, ARMCX1, ROCK1, PEG3, SFRP1, and CCND2.

The set of the regulatory regions of the following genes will be called OC Set3: CYP39A1, DAPK1, CAV1, ARMCX1, and ROCK1.

The set of the regulatory regions of the following genes will be called OC Set4: CYP39A1, DAPK1, CAV1, ARMCX1, and CDKN1B.

The set of the regulatory regions of the following genes will be called OC Set5: CYP39A1, DAPK1, CAV1, ARMCX1, and MLH1.

The set of the regulatory regions of the following genes will be called OC Set6: CYP39A1, DAPK1, CAV1, ARMCX1, and MED1.

The set of the regulatory regions of the following genes will be called OC Set7: CYP39A1, DAPK1, CAV1, ARMCX1, and BEX4.

EXAMPLES 653 publications related to gene methylation in ovarian cancers (OCs) were analyzed using an in-house developed literature/text mining tool, Dragon Exploration System. This analysis suggested 720 human genes and proteins being methylated in OC. Additionally, a list of genes methylated in OC was extracted from two gene methylation-related databases, MethyCancer and DiseaseMeth. These lists of genes were pooled and further complemented with the hyper-methylated genes from 484 publications reporting genes identified as hyper-methylated in tumor of OC patients when compared to normal tissues. For this pooled gene data we searched for information about gene expression in available public datasets.

The expression level of a number of these so-identified genes were found in two independent studies. The first study assessed the expression of these genes in 20 normal subjects with normal stroma and normal surface epithelial cells compared to 25 patients with ether cancer stroma or cancer epithelial cells. See Lili L N, Matyunina L V, Walker L D, Benigno B B, McDonald J F, "Molecular Profiling provides evidence of the existence of two functionally distinct classes of ovarian cancer stroma," submission date Jun. 12, 2012, and retrieved from the following address: www.ncbi.nlm-.nih.gov/geo/query/acc.cgi?acc=GSE38666, and which is incorporated by reference in its entirety.

The second study assessed in 12 subjects with normal surface epithelial cells compared to 12 patients with cancer epithelial cells. See Bowen N J, Walker L D, Matyunina L V, Logani S et al. Gene expression profiling supports the hypothesis that human ovarian surface epithelia are multi-potent and capable of serving as ovarian cancer initiating cells. BMC Med Genomics 2009 Dec. 29; 2:71. PMID: 20040092, which is incorporated by reference in its entirety.

Pooling together the data from the two studies and using computational methods, the methylation level (in serum samples) was inferred for each of the found genes in the 37 ovarian cancer patients and the 32 normal (cancer-free) subjects. From the found genes, the 20 top ranked ones were selected as those that manifested the greatest potential as screening markers for OC (the OC base set), even in presence of a substantial noise that we include in the model.

Table 1 (parts 1 and 2) present the predicted methylation calls from the 37 ovarian cancer patients. Values shown: the calls for the 37 OC patients, defined as: "TRUE": the serum predicted methylation value is above the threshold plus error margin of 33%; "FALSE": the serum predicted methylation value is below the threshold. The predicted methylation profile of combination of 20 biomarkers described in the table suggests 94.5% sensitivity and 100% of specificity when asking at least four "TRUE" calls to be diagnosed as having OC. When asking for at least one "TRUE" call to be diagnosed as having OC, then sensitivity increases to 97.2% while specificity remains 100%.

TABLE 1

|  | CYP39A1 (51302)[1] | DAPK1 (1612) | CAV1 (857) | ARMCX1 (51309) | ROCK1 (6093) | CDKN1B (1027) | MLH1 (1027) | MED1 (5469) | PEG3 (5178) | BEX4 (56271) |
|---|---|---|---|---|---|---|---|---|---|---|
| GSM359984 | TRUE | FALSE | TRUE | TRUE | FALSE | TRUE | FALSE | FALSE | TRUE | FALSE |
| GSM360039 | TRUE | TRUE | TRUE | FALSE | FALSE | FALSE | FALSE | TRUE | TRUE | FALSE |
| GSM360040 | TRUE | TRUE | TRUE | TRUE | TRUE | TRUE | TRUE | FALSE | TRUE | FALSE |
| GSM360041 | TRUE | TRUE | TRUE | TRUE | FALSE | FALSE | FALSE | TRUE | FALSE | FALSE |
| GSM360042 | TRUE | TRUE | FALSE | FALSE | FALSE | FALSE | FALSE | FALSE | FALSE | FALSE |
| GSM360043 | TRUE | FALSE | TRUE | TRUE | TRUE | TRUE | TRUE | FALSE | TRUE | TRUE |
| GSM360044 | TRUE | TRUE | TRUE | TRUE | TRUE | TRUE | TRUE | FALSE | FALSE | TRUE |
| GSM360045 | TRUE | TRUE | TRUE | FALSE | TRUE | FALSE | FALSE | TRUE | FALSE | FALSE |
| GSM360046 | TRUE | TRUE | TRUE | FALSE | TRUE | TRUE | TRUE | TRUE | FALSE | FALSE |
| GSM360047 | TRUE | TRUE | TRUE | FALSE | FALSE | FALSE | FALSE | FALSE | FALSE | FALSE |
| GSM360048 | TRUE | TRUE | TRUE | TRUE | TRUE | TRUE | TRUE | TRUE | FALSE | TRUE |
| GSM360049 | TRUE | FALSE | TRUE | TRUE | FALSE | TRUE | TRUE | FALSE | FALSE | TRUE |
| GSM947289 | FALSE | FALSE | FALSE | FALSE | FALSE | FALSE | FALSE | FALSE | FALSE | FALSE |
| GSM947290 | TRUE | TRUE | FALSE | FALSE | FALSE | FALSE | FALSE | FALSE | TRUE | FALSE |
| GSM947291 | TRUE | FALSE | TRUE | TRUE | TRUE | FALSE | FALSE | FALSE | FALSE | TRUE |
| GSM947292 | TRUE | TRUE | TRUE | TRUE | FALSE | FALSE | TRUE | TRUE | TRUE | TRUE |
| GSM947293 | TRUE | TRUE | TRUE | TRUE | TRUE | FALSE | TRUE | TRUE | TRUE | TRUE |
| GSM947294 | FALSE | FALSE | FALSE | FALSE | FALSE | FALSE | FALSE | FALSE | FALSE | FALSE |
| GSM947295 | TRUE | TRUE | FALSE | TRUE | FALSE | FALSE | FALSE | FALSE | FALSE | FALSE |
| GSM947296 | TRUE | TRUE | FALSE | TRUE | FALSE | FALSE | FALSE | FALSE | FALSE | FALSE |
| GSM947297 | TRUE | FALSE | TRUE | TRUE | TRUE | TRUE | TRUE | FALSE | TRUE | TRUE |
| GSM947298 | TRUE | TRUE | TRUE | TRUE | TRUE | TRUE | TRUE | FALSE | FALSE | TRUE |
| GSM947299 | TRUE | FALSE | TRUE | TRUE | FALSE | TRUE | FALSE | FALSE | TRUE | FALSE |
| GSM947300 | TRUE | TRUE | TRUE | TRUE | FALSE | FALSE | FALSE | FALSE | TRUE | FALSE |
| GSM947301 | TRUE | TRUE | TRUE | TRUE | TRUE | TRUE | TRUE | FALSE | TRUE | FALSE |
| GSM947302 | TRUE | TRUE | TRUE | TRUE | TRUE | FALSE | FALSE | FALSE | FALSE | FALSE |
| GSM947303 | TRUE | TRUE | TRUE | TRUE | FALSE | FALSE | FALSE | TRUE | FALSE | FALSE |
| GSM947304 | TRUE | TRUE | TRUE | TRUE | TRUE | TRUE | TRUE | TRUE | FALSE | TRUE |
| GSM947305 | TRUE | TRUE | TRUE | FALSE | TRUE | TRUE | TRUE | TRUE | TRUE | FALSE |
| GSM947306 | TRUE | TRUE | TRUE | FALSE | TRUE | FALSE | FALSE | TRUE | FALSE | FALSE |

TABLE 1-continued

| | | | | | | | | | |
|---|---|---|---|---|---|---|---|---|---|
| GSM947307 | TRUE | TRUE | FALSE | TRUE | FALSE | TRUE | TRUE | FALSE | TRUE | TRUE |
| GSM947308 | TRUE | TRUE | TRUE | TRUE | FALSE | TRUE | TRUE | TRUE | FALSE | FALSE |
| GSM947309 | TRUE | TRUE | TRUE | FALSE | FALSE | FALSE | FALSE | FALSE | FALSE | FALSE |
| GSM947310 | TRUE | TRUE | TRUE | FALSE | TRUE | FALSE | FALSE | FALSE | FALSE | FALSE |
| GSM947311 | TRUE | TRUE | TRUE | TRUE | TRUE | TRUE | TRUE | TRUE | FALSE | TRUE |
| GSM947312 | FALSE | TRUE | FALSE | TRUE | FALSE | FALSE | FALSE | TRUE | FALSE | FALSE |
| GSM947313 | TRUE | TRUE | TRUE | TRUE | TRUE | TRUE | TRUE | TRUE | TRUE | TRUE |

| | SFRP1 (6422)[1] | CCND2 (894) | SPARCL1 (8404) | ARMCX2 (9823) | PLAGL1 (5325) | RAD51C (5889) | SOCS2 (8835) | RARRES1 (5918) | UCHL1 (7345) | DIRAS3 (9077) |
|---|---|---|---|---|---|---|---|---|---|---|
| GSM359984 | TRUE | FALSE | FALSE | FALSE | FALSE | FALSE | FALSE | FALSE | FALSE | FALSE |
| GSM360039 | FALSE | FALSE | FALSE | FALSE | FALSE | TRUE | FALSE | FALSE | FALSE | FALSE |
| GSM360040 | TRUE | TRUE | TRUE | FALSE | TRUE | TRUE | FALSE | FALSE | FALSE | TRUE |
| GSM360041 | TRUE | TRUE | TRUE | FALSE | TRUE | TRUE | FALSE | FALSE | TRUE | FALSE |
| GSM360042 | TRUE | TRUE | FALSE | FALSE | FALSE | FALSE | TRUE | FALSE | FALSE | FALSE |
| GSM360043 | FALSE | FALSE | TRUE | FALSE | FALSE | FALSE | FALSE | FALSE | FALSE | TRUE |
| GSM360044 | FALSE | FALSE | FALSE | FALSE | FALSE | TRUE | FALSE | TRUE | TRUE | FALSE |
| GSM360045 | TRUE | FALSE | FALSE | FALSE | FALSE | TRUE | TRUE | FALSE | TRUE | FALSE |
| GSM360046 | FALSE | FALSE | FALSE | TRUE | FALSE | FALSE | FALSE | FALSE | FALSE | TRUE |
| GSM360047 | TRUE | TRUE | FALSE | FALSE | TRUE | FALSE | TRUE | FALSE | FALSE | FALSE |
| GSM360048 | FALSE | TRUE | FALSE | TRUE | FALSE | FALSE | FALSE | TRUE | FALSE | FALSE |
| GSM360049 | FALSE | TRUE | FALSE | TRUE | FALSE | FALSE | FALSE | FALSE | FALSE | FALSE |
| GSM947289 | FALSE | FALSE | FALSE | FALSE | FALSE | FALSE | FALSE | FALSE | FALSE | FALSE |
| GSM947290 | FALSE | FALSE | FALSE | FALSE | FALSE | TRUE | FALSE | FALSE | FALSE | FALSE |
| GSM947291 | FALSE | FALSE | FALSE | TRUE | FALSE | TRUE | FALSE | TRUE | TRUE | FALSE |
| GSM947292 | FALSE | FALSE | TRUE | FALSE | FALSE | FALSE | FALSE | FALSE | FALSE | FALSE |
| GSM947293 | TRUE | FALSE | FALSE | FALSE | FALSE | FALSE | FALSE | FALSE | FALSE | FALSE |
| GSM947294 | FALSE | FALSE | FALSE | FALSE | FALSE | FALSE | FALSE | FALSE | TRUE | FALSE |
| GSM947295 | FALSE | FALSE | FALSE | FALSE | FALSE | FALSE | FALSE | FALSE | FALSE | TRUE |
| GSM947296 | TRUE | TRUE | FALSE | FALSE | FALSE | FALSE | TRUE | FALSE | FALSE | FALSE |
| GSM947297 | FALSE | FALSE | TRUE | FALSE | FALSE | FALSE | FALSE | FALSE | FALSE | TRUE |
| GSM947298 | FALSE | FALSE | TRUE | FALSE | FALSE | FALSE | FALSE | TRUE | TRUE | FALSE |
| GSM947299 | TRUE | FALSE | FALSE | FALSE | FALSE | FALSE | TRUE | FALSE | FALSE | FALSE |
| GSM947300 | FALSE | FALSE | FALSE | FALSE | TRUE | FALSE | FALSE | FALSE | FALSE | FALSE |
| GSM947301 | TRUE | TRUE | TRUE | FALSE | TRUE | FALSE | FALSE | FALSE | FALSE | TRUE |
| GSM947302 | TRUE | FALSE | FALSE | FALSE | FALSE | FALSE | TRUE | FALSE | TRUE | FALSE |
| GSM947303 | TRUE | TRUE | TRUE | FALSE | TRUE | FALSE | TRUE | FALSE | TRUE | FALSE |
| GSM947304 | FALSE | TRUE | FALSE | TRUE | FALSE | FALSE | TRUE | TRUE | FALSE | FALSE |
| GSM947305 | FALSE | FALSE | FALSE | TRUE | FALSE | FALSE | FALSE | FALSE | FALSE | TRUE |
| GSM947306 | FALSE | FALSE | TRUE | FALSE | FALSE | FALSE | FALSE | TRUE | FALSE | FALSE |
| GSM947307 | FALSE | TRUE | FALSE | TRUE | FALSE | FALSE | FALSE | FALSE | FALSE | FALSE |
| GSM947308 | FALSE | FALSE | TRUE | FALSE | TRUE | TRUE | FALSE | TRUE | FALSE | FALSE |
| GSM947309 | TRUE | TRUE | FALSE | FALSE | TRUE | FALSE | TRUE | FALSE | FALSE | FALSE |
| GSM947310 | FALSE | FALSE | FALSE | FALSE | FALSE | FALSE | FALSE | FALSE | FALSE | FALSE |
| GSM947311 | FALSE | FALSE | FALSE | TRUE | TRUE | FALSE | FALSE | TRUE | FALSE | FALSE |
| GSM947312 | FALSE | FALSE | FALSE | FALSE | FALSE | TRUE | FALSE | FALSE | FALSE | FALSE |
| GSM947313 | FALSE | FALSE | TRUE | TRUE | FALSE | FALSE | FALSE | FALSE | FALSE | FALSE |

[1]Numbers in parentheses are NCBI Gene ID numbers.

From this base set of genes, several useful subsets of genes were identified:

OC Set1: CYP39A1, DAPK1, CAV1, ARMCX1, ROCK1, MED1, SFRP1, and CCND2.

OC Set2: CYP39A1, DAPK1, CAV1, ARMCX1, ROCK1, PEG3, SFRP1, and CCND2.

OC Set3: CYP39A1, DAPK1, CAV1, ARMCX1, and ROCK1.

OC Set4: CYP39A1, DAPK1, CAV1, ARMCX1, and CDKN1B.

OC Set5: CYP39A1, DAPK1, CAV1, ARMCX1, and MLH1.

OC Set6: CYP39A1, DAPK1, CAV1, ARMCX1, and MED1.

OC Set7: CYP39A1, DAPK1, CAV1, ARMCX1, and BEX4.

Other embodiments are within the scope of the following claims.

What is claimed is:

1. A method comprising:
   measuring, in a DNA sample from ovarian stroma, ovarian surface epithelial cells, or both, a methylation level in a CpG promoter island of each gene in a set of genes, wherein the set of genes consists of CYP39A1, DAPK1, CAV1, ARMCX1, ROCK1, MED1, SFRP1, and CCND2, and optionally any one or more of CDKN1B, MLH1, MED1, PEGS, BEX4, SPARC11, ARMCX2, PLAGL1, RAD51C, SOCS2, RARRES1, UCHL1 and DIRAS.

2. The method of claim 1, wherein the methylation level is determined by methylation-specific PCR.

* * * * *